US009375318B2

(12) United States Patent
Linares et al.

(10) Patent No.: US 9,375,318 B2
(45) Date of Patent: Jun. 28, 2016

(54) MULTI-COMPONENT KNEE IMPLANT ASSEMBLY WITH COMBINED ARTICULATING AND BELT SUPPORT AND TRAVELING SURFACES

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 163 days.

(21) Appl. No.: 14/281,438

(22) Filed: May 19, 2014

(65) Prior Publication Data
US 2014/0257503 A1    Sep. 11, 2014

Related U.S. Application Data

(62) Division of application No. 13/597,417, filed on Aug. 29, 2012, now Pat. No. 8,753,403.

(60) Provisional application No. 61/528,904, filed on Aug. 30, 2011.

(51) Int. Cl.
*A61F 2/38* (2006.01)
*A61F 2/30* (2006.01)

(52) U.S. Cl.
CPC .................. *A61F 2/3836* (2013.01); *A61F 2/38* (2013.01); *A61F 2002/30474* (2013.01); *A61F 2002/30639* (2013.01); *A61F 2002/30899* (2013.01); *A61F 2002/3895* (2013.01)

(58) Field of Classification Search
CPC ............ A61F 2/38; A61F 2002/30474; A61F 2002/30639
See application file for complete search history.

(56) References Cited

U.S. PATENT DOCUMENTS

| 5,480,443 | A | 1/1996 | Elias |
| 5,514,183 | A | 5/1996 | Epstein et al. |
| 6,117,175 | A | 9/2000 | Bosredon |
| 8,702,800 | B2 | 4/2014 | Linares et al. |
| 8,702,802 | B2 | 4/2014 | Linares et al. |
| 2010/0191342 | A1 | 7/2010 | Byrd et al. |

FOREIGN PATENT DOCUMENTS

| EP | 1228739 A2 | 8/2002 |
| WO | 9800076 A1 | 1/1998 |
| WO | 2004080331 A2 | 9/2004 |
| WO | 2009039164 A1 | 3/2009 |

OTHER PUBLICATIONS

Tan et al., "Developments of an Antimicrobial Microporous Polyurethane Membrane", Journal of Membrane Science, 289. 199-209 (2007).

*Primary Examiner* — Brian Dukert
(74) *Attorney, Agent, or Firm* — Dinsmore & Shohl LLP; Douglas J. McEvoy

(57) ABSTRACT

A joint assembly incorporated into reconditioned end surfaces established between an upper bone and an opposing lower bone. The assembly includes a pair of first components anchored into reconditioned bone end surfaces of a first joint defining bone and exhibiting a flexible and band-shaped loop displace-ably supported along exposed undersides established between outer portions which are assembled around the bands. A second component anchored into a second reconditioned end surface of a second joint defining bone exhibits a planar support surface upon which said bands are in contact with and displace during articulating motion of the bones. Entrapment pockets are formed within the first components for collecting wear particles and debris resulting from displacement of the belt.

19 Claims, 4 Drawing Sheets

MULTI-COMPONENT KNEE IMPLANT ASSEMBLY WITH COMBINED ARTICULATING AND BELT SUPPORT AND TRAVELING SURFACES

CROSS-REFERENCE TO RELATED APPLICATIONS

This Application is a Division of application Ser. No. 13/597,417 filed on Aug. 29, 2012. Application Ser. No. 13/597,417 claims the benefit of U.S. Provisional Application 61/528,904 filed on Aug. 30, 2011, the contents of which are incorporated herein in their entirety.

FIELD OF THE INVENTION

The present invention discloses an artificial joint assembly, such as is particularly configured for employing as a retrofit knee joint, and which combines pairs of end anchored artificial components incorporated into each of first and second reconditioned joint defining surfaces for providing increased wear life in tandem with evenly distributed wear pattern/profile as well as enhanced flexibility and mobility.

BACKGROUND OF THE INVENTION

The prior art is well documented with examples of artificial knee implant assemblies. These include such as the spherical knee joint prosthesis of Bosredon, U.S. Pat. No. 6,117,175, the total knee implant of Byrd et al., US 2010/0191342 and the artificial implant component and method for securing disclosed in Elias, U.S. Pat. No. 5,480,443.

SUMMARY OF THE INVENTION

The present invention discloses a joint assembly incorporated into reconditioned end surfaces established between an upper bone and an opposing lower bone. The assembly includes a first component anchored into a first of the reconditioned bone end surfaces and exhibiting a first exposed support surface and a second component anchored into a second of the reconditioned bone end surfaces and exhibiting a second exposed support surface further including a flexible and conveyable closed loop belt relatively displaceable upon contact with the first support surface.

At least one of the components may further exhibit an arcuate shaped support surface and can be constructed of at least one of a metal, plastic, polymer or composite material. In one desired arrangement, a first pair of components are arranged at a first side of said assembly affixed to reconditioned opposing surfaces associated with first and second knee joint defining bones, with a second identical pair arranged at an opposite second side. This can further include a ½ implant assembly associated with a selected side of the joint defining bones, and such as in combination with a natural remaining portion of the joint.

The second component may further incorporate a subassembly including a pair of side assembleable outer portions capturing the belt therebetween such that an upper portion of said belt is exposed for contacting said first component. Each of the side assembleable outer portions further includes opposing and mating receiving channels for supported the belt in conveyable fashion therebetween. The side assembleable outer portions each may also include aligning tab and slot portions for inter-assembling about the belt.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit knee joint, and which combines respective upper and lower pairs of artificial components incorporated into first and second reconditioned joint defining surfaces, such as for providing increased wear life along with both enhanced flexibility and mobility.

The joint assemblies described herein are particularly configured for such as in situ reconditioned installation within a patient's knee assembly (between the lower end of the upper femur bone and corresponding upper end of the lower tibia bone), however it is further understood that certain applications could in theory include other joint applications, either human or other mammalian. For purposes of ease and clarify of illustration, the various embodiments depicted further do not include reference to additional necessary components of the knee joints, such as including the patella (knee cap) and associated muscles, tendons and ligaments, the inclusion of which are assumed and which collectively define a functioning knee joint.

Figure 1:
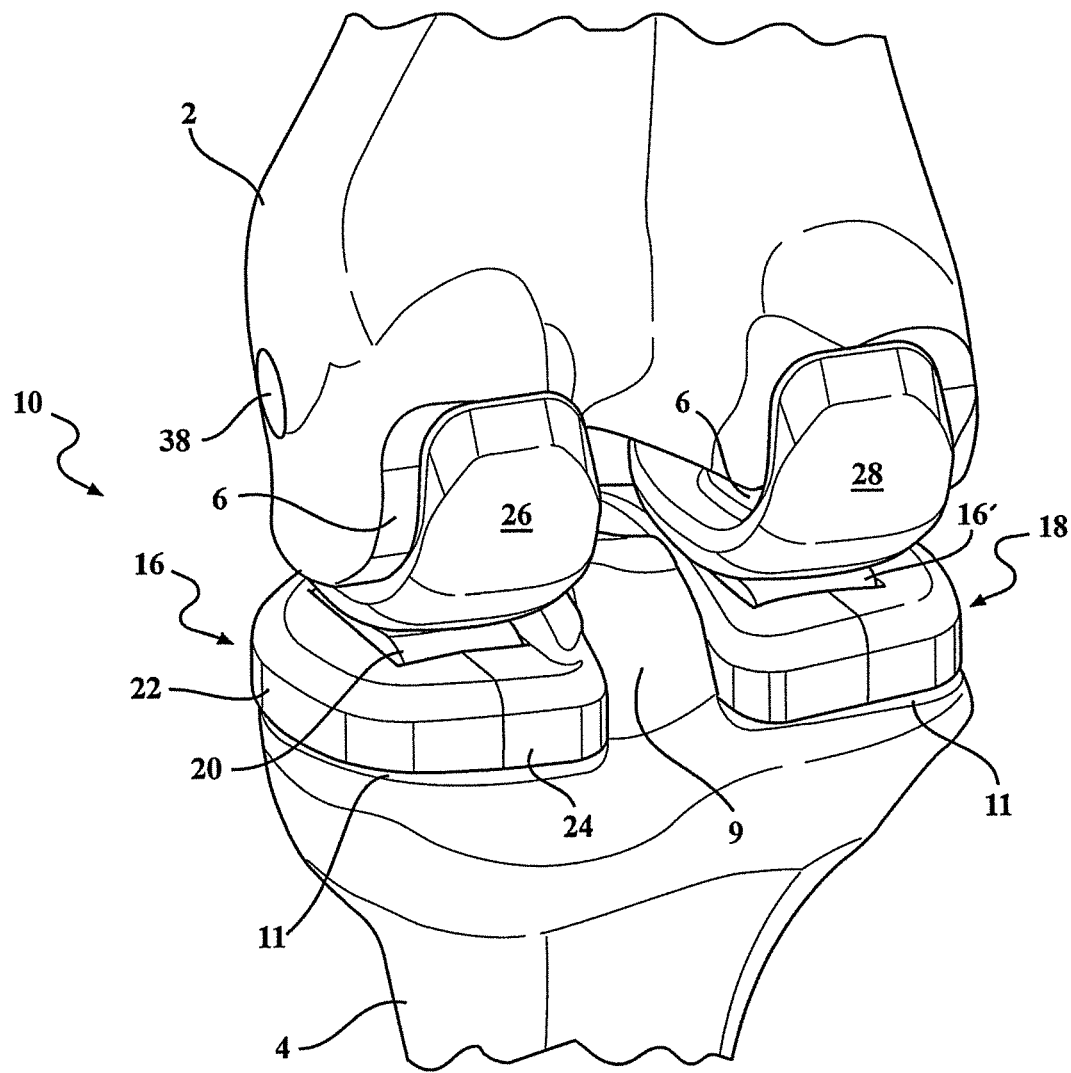
FIG. 1 is a perspective view of a knee implant assembly according to a first embodiment of the invention.

Referring now to FIG. 1, a perspective view is generally shown at 10 of a knee implant assembly according to a first embodiment of the invention and which is incorporated between an upper leg (femur) bone 2 and a lower leg (tibia) bone 4 (and with which an associated fibula bone is also not depicted). The present invention contemplates such as in situ reconditioning of the bone ends, illustrated by conditioned end profiles 6 configured into the bottom most end surface of the femur 2, as well as opposing upper end facing and recessed profiles 8 defined in the upper most end of tibia 4 with additional bridging location 9 defined between the substantially hemispherical shaped recessed profiles 8.

Figure 2:
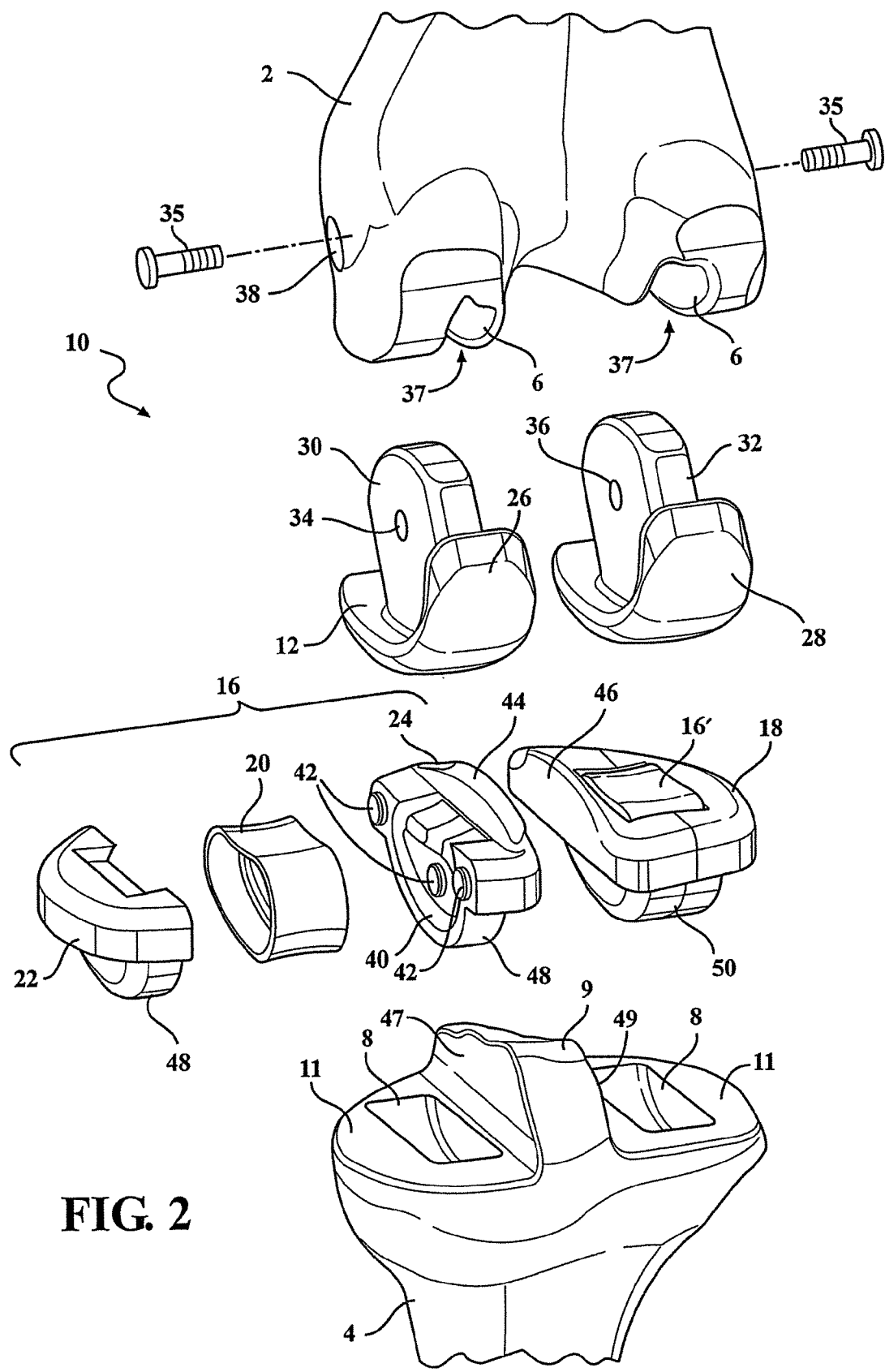
FIG. 2 is an exploded view of the multi-component assembly of FIG. 1 and better illustrating the reconditioned end-configurations established between the upper femur and lower tibia leg bones combined with the pairs of upper bone secured arcuate portions and lower bone secured conveyor belt and supporting portions, a selected one of which is further depicted in subassembly exploded fashion to better illustrate the configuration of the inner conveying belt and outer side assembleable body portions.

As best shown in FIG. 2, the recesses 8 are depicted by a spaced apart pair of generally three dimensional semi-circular profiles each including an arcuate recessed profile bounded along opposites sides by planar parallel spaced end walls as shown and which are established at right and left sides of the joint zone. The recessed profiles 8 are defined in reconditioned flat surfaces 11 which are separated by the intermediate bridging location 9.

Such reconditioning occurs following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle associated with a normal functioning joint.

Although not shown, such reconditioning can be employed with minimal interference to such necessary additional elements of the joint including each of the patella or knee cap, ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total (or paired) or partial (one side or one half of the joint) manner concurrent with any necessary degree of refashioning or removal of damaged bone or joint.

Referring to FIG. 1 again in collaboration with exploded view of FIG. 2, the multi-component assembly 10 better illustrates the reconditioned end-configurations 6 and 8 established between the upper femur 2 and lower tibia 4 leg bones, combined with each of a pair of upper bone secured arcuate (or track) portions 12 and 14 and lower bone secured and conveyor belt integrated subassemblies 16 and 18. A selected subassembly 16 is further depicted in subassembly exploded fashion to better illustrate the configuration of an inner conveying belt 20 and outer side assembleable body portions 22 and 24, with corresponding subassembly 18 depicted in assembled fashion but being identical in construction.

Each of the components 12-18 are constructed of any arrangement of metal, polymer, plastic, composite or other suitable material, with it further being understood that the individual pairs of components can be arrayed with any pattern of alternating materials. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

Both the upper bone secured arcuate (or track) portions 12 and 14 and lower bone belt supporting subassemblies 16 and 18 are anchored in seating fashion within the inner recessed profiles 6 and 8 of the femur 2 and tibia 4 bones, respectively, by use of a suitable medical cement (it further being understood that suitable bone adhesion can also be assisted or promoted by inner marrow in given circumstances). The upper track portions 12 and 14 each exhibit and arcuate exposed surface (see at 26 and 28 in FIG. 2), with inner (reverse side) extending stems 30 and 32 being recess mounting within the mating recess configurations 6 defined in the joint end defining face of the upper femur bone 2.

Width extending apertures 34 and 36 are further defined in the stems 30 and 32 and can also receive like widthwise inserting pins 35, upon installation of the track portions as depicted by arrows 37. The pins 35 extend through mating and aligning apertures formed widthwise through the femur bone 2 (see further at 38) to further affix the track portions 12 and 14 within the joint end defined surface in the femur bone 2.

The lower bone secured belt conveyor and support subassemblies 16 and 18 each further exhibit an inner flexible and closed looped band (see again selected band shaped belt 20 depicted in exploded fashion with respect to exploded subassembly 16 with an identical such band 16' depicted for corresponding assembled subassembly 18. The outer assembleable portions 22 and 24 (typically a harder plastic as opposed to the inter-disposed flexible band 20) each exhibit opposing receiving channels (see as shown at 40 for selected assembleable side portion 24 with opposing and mating receiving cannel for portion 22 being hidden from view) and are inter-assembled with the band 20 supported therebetween in conveyable fashion therebetween.

Opposing pairs of tab and slot or other suitable fasteners are provided on inside faces of the outer support portions 22 and 24 (see as further depicted at 42 disposed upon inside facing surface of side portion 24, with mating receiving locations in opposing support portion 22 again hidden from view). Additional projecting edge locations 44 and 46 are defined on opposing inner surfaces of the support subassemblies and abut against configured sides 47 and 49 (again FIG. 2) of the bridging location 9 of the refashioned end surface of the lower tibia 4 combined with additional bottom convex surfaces 48 and 50 seating within the afore-described mating recessed profiles 8 associated with the refashioned tibia end face.

In this fashion, the path of travel of the upper portion arcuate exposed surfaces 26 and 28 causes the belts 20 to be fairly easily displaced along the tracks defined between the side assembleable supports 22 and 24 and in such a fashion that ease of bending motion is achieved for the joint assembly. As again previously indicated, additional configurations of muscles, ligaments, tendons and patella (knee cap) are provided and can include both natural and/or synthetic materials which can be implanted or reconstructed in order to provide a dynamic and long-term implantable assembly.

Figure 5:
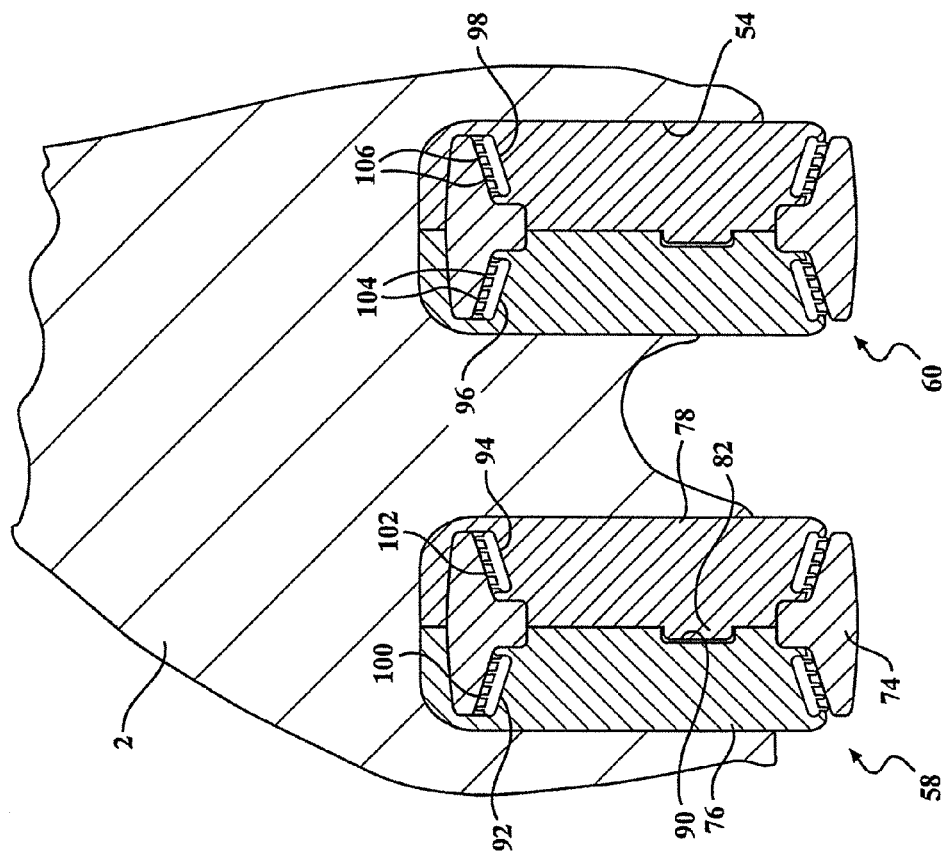
FIG. 5 is a plan cutaway of such as the upper bone in FIG. 3 and better illustrating the three piece construction of the side by side arranged pair of conveyor belt and support portions and including debris entrapment pockets defined in surface locations of the mating support portions arranged on an underside of the intermediate supported conveyor belt.
Figure 3:
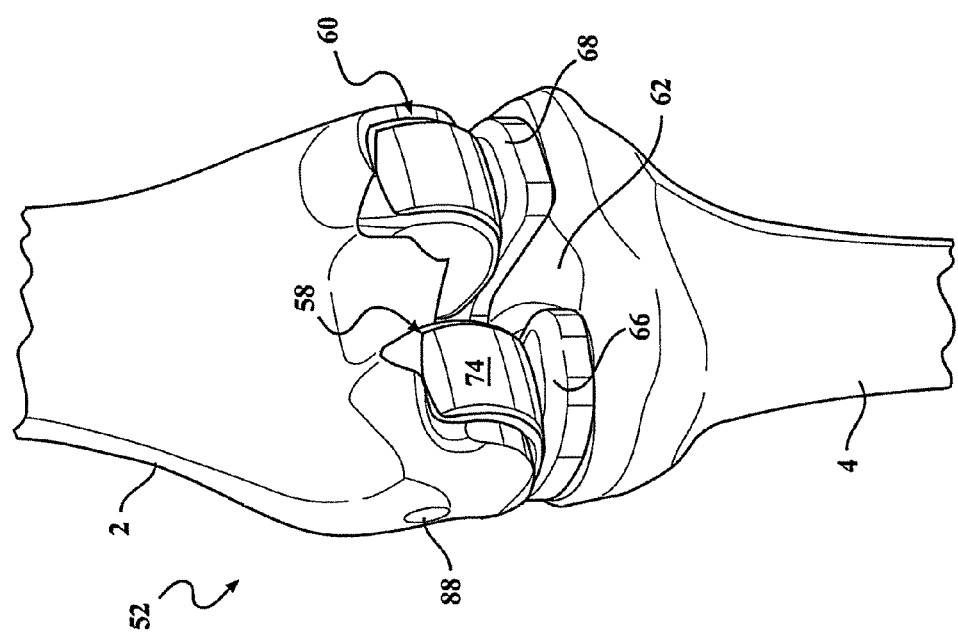
FIG. 3 is an illustration of a knee implant assembly according to a further preferred variant.
Figure 4:
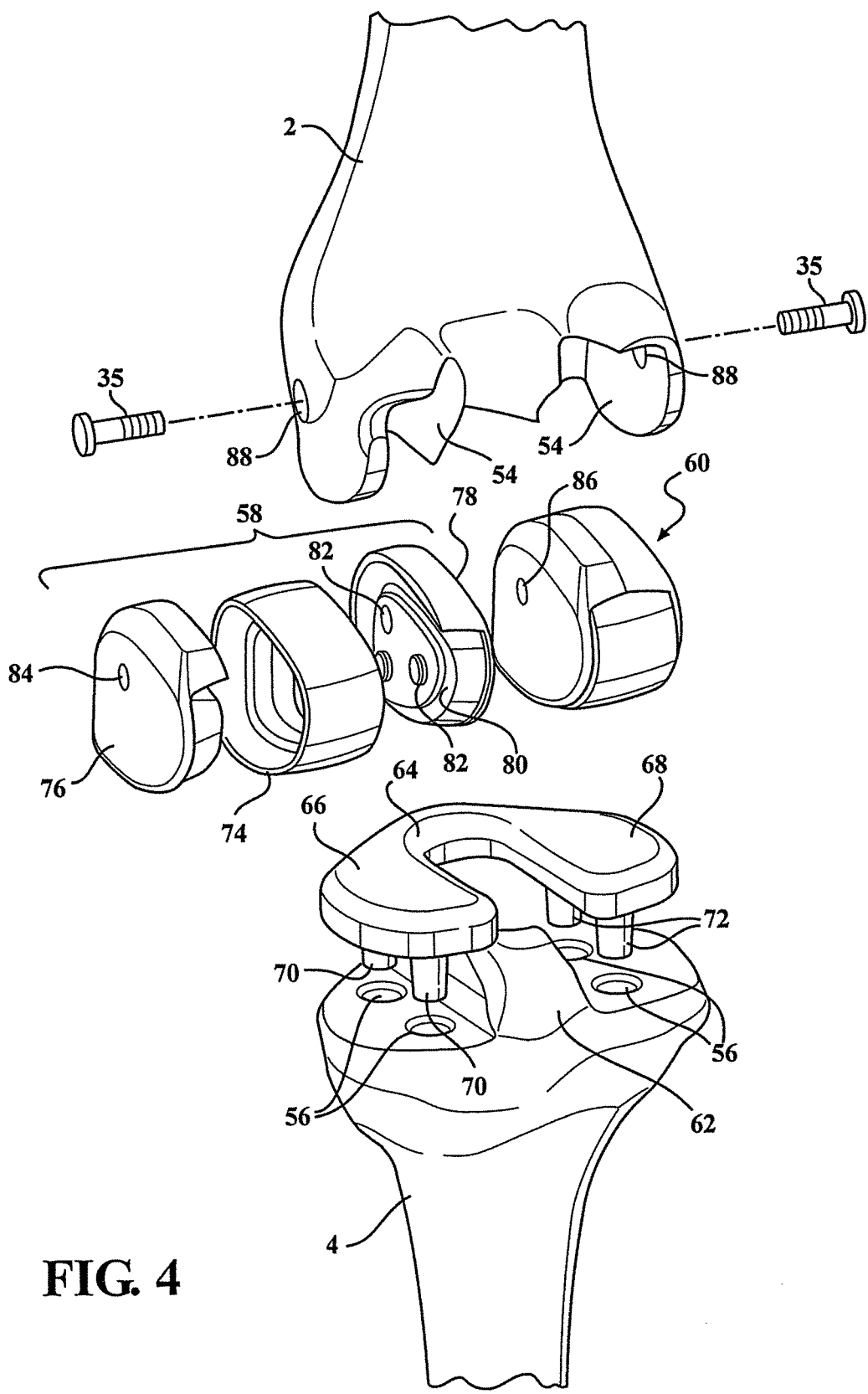
FIG. 4 is an exploded view of the assembly of FIG. 3 and better illustrating the further reconditioned end-configurations established between the upper femur and lower tibia leg bones combined with the pairs of upper bone secured conveyor belt and supporting portions combined with the lower bone secured platform support for receiving the exposed conveyor belt portions.

Proceeding to FIGS. 3-5 in succession, respective perspective, exploded and plan cutaway views are provided of knee implant assembly according to a further preferred variant and as generally depicted at 52. As best shown in FIG. 4, a different set of reconditioned and recess configured profiles are fashioned within the joint end faces of the femur 2 and tibia 4, and are defined respectively at 54 and 56, respectively and in comparison to the configuration of the corresponding profiles 6 and 8 in FIG. 2.

The upper recess profiles 54 each exhibit a substantially three dimensional shaped cavity for receiving a pair of individual shaped bodies including upper conveyor and lateral assembleable supporting portions (see as defined by individual exploded subassembly 58 and further assembled subassembly 60). The lower recess profiles 56 each define a pair of inwardly recessed holes exhibited on sides of a generally planar shaped refashioned end face of the lower tibia bone, with the refashioned projecting bridging portion established therebetween at 62.

A one piece support platform 64 exhibits a modified U shape with a narrow intermediate bridging location and widened side ear or lobe surfaces 66 and 68. Additional pairs of extending posts 70 and 72 are integrally disposed with integrally defined and underside projecting locations of the platform 64 and such that the posts are anchored (cemented) into the bone end surface refashioned recesses 56 in a manner which permits the platform 64 to be secured thereupon, such as further depicted in FIG. 3.

The construction of the belt conveyor and side assembled support subassemblies 58 and 60 is largely the same as previously referenced as to corresponding subassemblies 16 and 18 in FIG. 2, with the exception that the belt and support assemblies are anchored within an underside of the upper femur bone 2 as opposed to the upper joint defining face of the lower tibia bone 4 as in FIGS. 1 and 2. Similar to the first preferred embodiment, and referring to selected exploded subassembly 58 in FIG. 4, a flexible and band shaped loop or belt 74 is configured for mounting within opposed assembling inner facing surfaces of outer assembleable supports 76 and 78, each of which again further defining inner receiving channels or guides (see at 80 for selected side support 78).

Additional tab and slot assembly locations, see as depicted by tabs 82 defined in exposed and selected side support 78 (with again mating slots associated with opposing face of support 76 hidden from view but depicted in reference to cutaway FIG. 5), and which facilitate inter-assembly of the side supports 76 and 78 in order to establish the three dimensional assembly further depicted by selected subassembly 60. To facilitate mounting, apertures 84 and 86 defined in widthwise extending fashion through the assembled subassemblies 58 and 50 align, upon installation of the subassemblies into the recessed end configurations 54 of the femur 2, with a further widthwise extending aperture 88, such as again for receiving a pin or the like (such as again depicted at 35) for further assisting in anchoring the displaceable belt supporting subassemblies 58 and 60 into position.

Referring finally to FIG. 5, a plan cutaway is shown of such as the upper femur bone 2 in FIG. 3 and better illustrating the three piece construction of the side by side arranged pair of conveyor belt and support portion subassemblies 58 and 60. The inter-engaging nature of the subassembly component halves, such as at 76 and 78, is better depicted in FIG. 5 and which illustrates receiving slots (see at 90) associated with selected side assembleable portion 76 (the inner facing side of which is hidden in FIG. 4) for receiving a selected and aligning tab 82.

Of particular note in FIG. 5, each of the subassemblies 58 and 60 include circumferential disposed pairs of debris entrapment pockets which are defined along inside surface locations of the side assembleable and mating support portions and such that the entrapment chambers or pockets are arranged along undersides of the intermediate supported and displaceable conveyor belts/bands. These are particularly shown at 92 and 94 arranged along inner sides of the flexible band 74 associated with belt conveyor subassembly 58 and further at 96 and 98 arranged along corresponding inner sides of the flexible band associated with the other belt conveyor subassembly 60.

Each of the entrapment pockets or chambers further include narrowed communicating locations 100, 102, 104 and 106 in relation to associated entrapment chambers 92, 94, 96 and 98 in contact with the inner displacing surfaces of the flexible bands (e.g. again as shown by example at 74) and which lead to an enlarged collecting reservoir for securely holding micron sized debris resulting from progress wear profiles along the joint assembly, and in particular wearing away of the translating belts over time. In this fashion, long term functionality is achievable for the joint assembly and without permitting the accumulating debris to otherwise compromise the functionality of the joint.

As previously explained, additional variants of the joint assemblies contemplate a first side or half being reconditioned in the manner depicted herein, with a further side or unreconstructed half retaining its original joint defining structure and which, to the extent possible, is unaffected by the reconditioning performed to the implanted half of the joint assembly.

Having described my invention, other and additional preferred embodiments will become apparent to those skilled in the art to which it pertains, and without deviating from the scope of the appended claims.

We claim:

1. A joint assembly incorporated into reconditioned end surfaces established between an upper bone and an opposing lower bone, said assembly comprising:
   a pair of first component subassemblies adapted to being anchored to reconditioned end surfaces of a first joint defining bone, each of said first component subassemblies having a flexible and band-shaped loop displaceably supported between a pair of outer assemble-able portions, such that exposed locations of said bands extend along open undersides established between said assemble-able outer portions; and
   a second component anchored into a second reconditioned end surface of a second joint defining bone, said second component exhibiting a planar support surface upon which said bands are in contact with and displace during articulating motion of said joint defining bones.

2. The joint assembly as described in claim 1, each of said pair of first components further exhibiting an arcuate shaped support surface.

3. The joint assembly as described in claim 1, each of said first and second components further being constructed of at least one of a metal, plastic, polymer or composite material.

4. The joint assembly as described in claim 1, each of said outer assemble-able portions further comprising opposing and mating receiving channels for supported said belt in displaceable fashion therebetween.

5. The joint assembly as described in claim 4, said outer assemble-able portions each further comprising aligning tab and slot portions for inter-assembling about said belt.

6. The joint assembly as described in claim 5, further comprising circumferential extending debris entrapment pockets along inside surface locations of said outer assemble-able portions and in communication with translating surfaces of said belts.

7. The joint assembly as described in claim 6, further comprising inner surfaces of each of said belts having narrowed locations communicating said belts with said entrapment pockets for collecting and holding debris resulting from progressive wearing of said belts.

8. The joint assembly as described in claim 1, said second component further comprising a generally "U" shape with underside projecting posts adapted to mount within aligning apertures defined in said second reconditioned bone end surface.

9. A process for in-situ reconditioning of opposing ends of femur and tibia joint defining bones and for installing into the reconditioned ends an artificial joint assembly, comprising the steps of:
   incising a patient location to access damaged opposing ends of the joint defining bones;
   removing damaged or detached portions of bone and cartilage;

refashioning each of the joint defining bone ends including forming at least one three dimensional recessed profile in each bone end;

installing a pair of first component subassemblies into a pair of refashioned profiles defined in the first of the reconditioned bone ends, such that anchoring portions of each of the first component subassemblies seats within the three dimensional recessed profile, the first component subassemblies each exhibiting a flexible and band-shaped loop displace-ably supported along exposed undersides established between outer portions which are assembled around said bands; and installing a second component into the other of the reconditioned bone ends such that an anchoring portion of the second component seats within the three dimensional recessed profile, the second component exhibiting a planar support surface upon which said bands are in contact with and displace during articulating motion of said joint defining bones.

10. The process as described in claim 9, said step of refashioning a first of said joint defining bone ends further comprising the step of forming a semicircular base surface bounded along opposite sides by a pair of planar and spaced apart end walls.

11. The process as described in claim 10, said step of installing a pair of first component subassemblies further comprising inserting a pair of pins in opposing and widthwise extending directions through apertures extending inwardly from opposite sides of the first joint defining bone and in communication with said three dimensional recessed profiles, said pins seating within aligning apertures defined in outer selected assembleable portions of each of said pair of first component subassemblies.

12. The process as described in claim 9, said step of refashioning a second of said joint defining bone ends further comprising fashioning a continuous planar surface along each of first and second sides of the bone and which is interconnected at a forward end, a refashioned bridging portion extending at a generally central location of the second bone end and around which is supported the second component.

13. The process as described in claim 12, said step of refashioning further comprising forming apertures in the planar reconditioned surfaces of the second bone end, these receiving underside extending mounting posts associated with said second component.

14. A joint assembly incorporated into reconditioned end surfaces established between an upper bone and an opposing lower bone, said assembly comprising:

at least one first component subassembly adapted to being anchored to a reconditioned end surface of a first joint defining bone, said first component subassembly having a flexible and band-shaped loop displace-ably supported between a pair of outer assemble-able portions, such that exposed locations of said band extends along open undersides established between said assemble-able outer portions, each of said outer assemble-able portions further having opposing and mating receiving channels for supported said belt in displaceable fashion therebetween; and a second component anchored into a second reconditioned end surface of a second joint defining bone, said second component exhibiting a planar support surface upon which said band is in contact with and displace during articulating motion of said joint defining bones.

15. The joint assembly as described in claim 14, said outer assemble-able portions each further comprising aligning tab and slot portions for inter-assembling about said belt.

16. The joint assembly as described in claim 15, further comprising circumferential extending debris entrapment pockets along inside surface locations of said outer assemble-able portions and in communication with translating surfaces of said belts.

17. The joint assembly as described in claim 16, further comprising inner surfaces of each of said belts having narrowed locations communicating said belts with said entrapment pockets for collecting and holding debris resulting from progressive wearing of said belts.

18. The joint assembly as described in claim 14, said second component further comprising a generally "U" shape with underside projecting posts adapted to mount within aligning apertures defined in said second reconditioned bone end surface.

19. The joint assembly as described in claim 1, the first joint defining bone further including a tibia bone and the second joint defining bone further including a femur bone, said pair of first component subassemblies adapted to being mounted atop reconditioned ends of the tibia bone in opposition to said second component mounted to the femur bone.

\* \* \* \* \*